United States Patent
Ruhlmann et al.

(10) Patent No.: US 12,043,693 B2
(45) Date of Patent: *Jul. 23, 2024

(54) THICKENING AGENT FOR AQUEOUS SYSTEMS, FORMULATIONS CONTAINING SAME AND USES THEREOF

(71) Applicant: COATEX, Genay (FR)

(72) Inventors: Denis Ruhlmann, Genay (FR); Catherine Corfias Zuccalli, Villeurbanne (FR); Jean-Marc Suau, Lucenay (FR); Yves Matter, Quincieux (FR); Benoit Magny, Cailloux sur Fontaines (FR)

(73) Assignee: COATEX, Genay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/304,283

(22) Filed: Jun. 17, 2021

(65) Prior Publication Data

US 2021/0309788 A1   Oct. 7, 2021

Related U.S. Application Data

(63) Continuation of application No. 15/747,014, filed as application No. PCT/FR2016/052022 on Aug. 3, 2016, now Pat. No. 11,066,505.

(30) Foreign Application Priority Data

Aug. 5, 2015  (FR) .................................. 1557551

(51) Int. Cl.
| | | |
|---|---|---|
| *C08G 18/28* | (2006.01) | |
| *A61K 8/87* | (2006.01) | |
| *C08G 18/48* | (2006.01) | |
| *C08G 18/72* | (2006.01) | |
| *C08G 18/75* | (2006.01) | |
| *C08L 75/08* | (2006.01) | |
| *C09D 5/14* | (2006.01) | |
| *C09D 7/43* | (2018.01) | |
| *C09D 7/47* | (2018.01) | |
| *C11D 3/37* | (2006.01) | |

(52) U.S. Cl.
CPC ....... *C08G 18/283* (2013.01); *C08G 18/4833* (2013.01); *C08G 18/72* (2013.01); *C08G 18/755* (2013.01); *C08L 75/08* (2013.01); *C09D 5/14* (2013.01); *C09D 7/43* (2018.01); *C09D 7/47* (2018.01); *A61K 8/87* (2013.01); *A61K 2800/48* (2013.01); *C08L 2201/54* (2013.01); *C11D 3/3726* (2013.01)

(58) Field of Classification Search
CPC .. C08G 18/283; C08G 18/4833; C08G 18/72; C08G 18/755; C08L 75/08; C08L 2201/54; C09D 5/14; C09D 7/43; C09D 7/47; A61K 8/87; A61K 2800/48; C11D 3/3726
See application file for complete search history.

(56) References Cited

U.S. PATENT DOCUMENTS

| | | | |
|---|---|---|---|
| 5,594,087 A | 1/1997 | Konig et al. | |
| 11,066,505 B2 * | 7/2021 | Ruhlmann | C09D 5/14 |
| 2007/0293625 A1 | 12/2007 | Sauer et al. | |
| 2011/0166291 A1 * | 7/2011 | Turk | C09D 7/43 |
| | | | 524/591 |
| 2012/0101170 A1 | 4/2012 | Turk | |
| 2013/0158160 A1 | 6/2013 | Suau | |

OTHER PUBLICATIONS

International Search Report issued Dec. 15, 2016 in PCT/FR2016/052022 filed Aug. 3, 2016.

* cited by examiner

*Primary Examiner* — Rabon A Sergent
(74) *Attorney, Agent, or Firm* — Oblon, McClelland, Maier & Neustadt, L.L.P.

(57) ABSTRACT

The present invention relates to novel associative thickeners pertaining to the HEUR category (Hydrophobically-modified Ethoxylated URethane), to intermediate aqueous formulations containing such thickeners, and to the final compositions, for example paint, lacquer, varnish or paper coating slip compositions.

20 Claims, No Drawings

THICKENING AGENT FOR AQUEOUS SYSTEMS, FORMULATIONS CONTAINING SAME AND USES THEREOF

CROSS REFERENCE TO RELATED APPLICATIONS

The present application is a Continuation of U.S. Ser. No. 15/747,014, filed Jan. 23, 2018, now allowed, which is a 371 of PCT/FR2016/052022, filed Aug. 3, 2016. The present application also claims priority to French application 1557551, filed Aug. 5, 2015.

The present invention relates to novel associative thickeners belonging to the category of the HEUR (Hydrophobically modified Ethoxylated URethanes). These products comprise an ethoxylated associative compound comprising a carbon-based chain end and at least one methyl and/or ethyl branching. The present invention also relates to intermediate formulations comprising such thickeners and to the use of these compounds as thickeners in final compositions, for example paint compositions.

Paints consist of fillers and pigments and at least one organic polymer known as binder. In addition to the fillers, the pigments and the binder, a paint composition also comprises a solvent (which is water in the case of aqueous-phase paints), additives for the rheology, additives for the stability (storage, formation of the film, UV) and other additives for obtaining special properties. The behaviour and the properties of the paints depend on the nature of their constituents, in particular of the binder, fillers and pigments and also rheological additives. They generally comprise one or more thickener(s), the role of which is to control the rheology of the compositions containing it/them, both at the stage of their manufacture and during their transportation, their storage or during their implementation. Given the diversity of the practical constraints at each of these stages, it is advantageous for the formulator to have available a range of thickeners having different rheological behaviours when they are used in the final compositions. In addition, these thickeners can confer additional properties on the compositions, for example on the paints, which contain them.

The following are distinguished among all the thickeners for paints:
- natural cellulose-based thickeners, also known as cellulose ethers, of HEC type or of HMHEC (Hydrophobically Modified HEC) type,
- acrylic thickeners of non-associative type, known as ASE (Alkali Swellable Emulsions) and those of associative type, known as HASE (Hydrophobically modified Alkali Swellable Emulsions) and
- associative thickening polyurethanes of HEUR (Hydrophobically modified Ethoxylated URethane) type.

The thickening polyurethanes or HEUR result from the condensation between a compound of poly(alkylene glycol) type, a polyisocyanate and an associative compound of alkyl, aryl or arylalkyl type consisting of a hydrophobic end group. Coatex is the source of numerous research studies on paint thickeners. Furthermore, Coatex markets the products of the Coapur® range, for example the Coapur® XS products, which are non-ionic thickening polyurethanes providing rheological profiles which vary between the newtonian type (low viscosity at low shear gradient) and/or the pseudoplastic type (high viscosity at low shear gradient).

The document U.S. Pat. No. 5,594,087 describes polyurethanes used as thickening agents for aqueous paint formulations, the rheological profile of which is balanced at low shear gradient and at high shear gradient.

The document US 2007 293625 describes the preparation of polyurethane thickening agents for aqueous compositions with an effect at a low shear gradient.

The inventors have developed a novel thickening polyurethane which makes it possible to very notably increase the viscosity at a high shear gradient and to thus confer, on the composition containing it, a good dynamic behaviour, that is to say a high viscosity at a high shear gradient, while maintaining a very good pigmentary compatibility. This thickener can be classified in the category of the thickeners of newtonian or "ICI builder" type.

A thickener of "ICI builder" type can be defined as a product which leads to an increase in the ICI viscosity when its dosage within the paint composition is increased.

This novel thickener can, for example, be used alone in a paint composition where it is necessary to have a high viscosity at a high shear gradient (for example a satin or gloss paint comprising a high latex content).

It can also be used in combination with a thickener of pseudoplastic type. Such a combination thus makes it possible to obtain a composition having a good dynamic behaviour related to the presence of the newtonian thickener and a good static behaviour related to the presence of the thickener of pseudoplastic type.

Such a thickener can be formulated in the aqueous phase and, as a result of its specific structure, it makes possible thickening of the final composition without requiring specific equipment or high shear energy.

This novel thickener has, at the chain ends, polyethoxylated hydrophobic groups of formula (I):

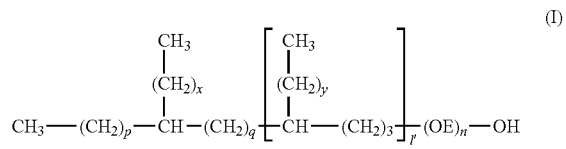

in which:
x and y represent, independently of one another, 0 or 1,
p, q, s and r are integers at least one of which is non zero,
$5 < p+x+q+2r+yr+rs < 11$ and
n represents an integer or a decimal number varying between 20 and 40.

The document WO 2011/104599 (Coatex) describes rheology-modifying polymers for aqueous systems, in particular paint formulations. The thickeners described, of acrylic thickener type, can in particular comprise ethyl acrylate (EA), methacrylic acid (MAA) and polymerizable monomer units of formula:

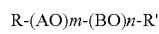

in which:
R designates a polymerizable unsaturated group, for example methacrylate,
A and B designate alkyl groups which are different from one another and which have from 2 to 4 carbon atoms, for example ethylene oxide and propylene oxide,
m and n are integers of less than 150 at least one of which is non zero and
R' consists of at least one group of the following formula:

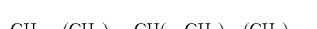

in which
p and q designate integers at least one of which is non zero and
$5<p+q<13$.

Such acrylic polymers have a different rheological profile from that of the thickeners of the present invention. Namely, they come within the category of acrylic thickeners of pseudoplastic type (high viscosity at low shear gradient).

The document CA 2,129,932 (Bayer), for its part, describes polyurethanes for thickening aqueous systems, these polyurethanes consisting of alcohol of formula $R_2$—O—$A_yH$ in which $R_2$ represents an aliphatic alcohol with from 16 to 22 carbon atoms.

Definitions

In the description of the present invention, the term "HEUR" is an acronym for "Hydrophobically modified Ethoxylated URethane".

In the description of the present invention, unless otherwise indicated, the percentages expressed represent percentages by weight and are expressed with respect to the total weight of the reference element. For example, when it is indicated that a polymer comprises 10% of a monomer or of a reactant, it is understood that the polymer comprises 10% by weight of this monomer or reactant, with respect to the total weight of this polymer.

In the description of the present invention, the expression "at least one" designates one or more compound(s) (for example one or more polyethoxylated alcohol compound(s), one or more polyol(s), one or more polyisocyanate(s)), such as a mixture of from 2 to 5 compounds.

"Alkyl" is understood to mean a linear or branched $C_xH_{2x+1}$ group, where x varies from 1 to 30, preferably from 10 to 30, indeed even from 12 to 28.

"Formulation" is understood to mean the thickening intermediate entity comprising the polyurethane agent according to the invention formulated in order to be easier to use in the final composition to be thickened. For example, the thickening agent according to the invention can be formulated in the presence of water and of surfactants in order to be more easily flowable/pourable and easier to incorporate in the composition to be thickened at room temperature. The viscosity of the formulation before its incorporation in the final aqueous composition is, for example, less than 10,000 mPa·s at 25° C. and at 100 revolutions per minute.

"Composition" is understood to mean the final entity to be thickened or the thickened final entity comprising the polyurethane agent according to the invention optionally formulated in the presence, for example, of water and of surface-active agents, and also all of its constituents, the list of which depends on the final application. For example, the final composition comprises inorganic pigments and binders, if it is a paint composition.

DETAILED DESCRIPTION OF THE INVENTION

The polyurethanes of the present invention are thickeners for aqueous compositions, for example aqueous paint compositions. They make it possible to obtain high viscosities at a high shear gradient and to thus confer, on the compositions, a good dynamic behaviour. These thickening polyurethanes can be categorized in the category of thickeners of newtonian or "ICI builder" type.

Some paint compositions, for example satin or gloss paints, which comprise few pigments (in comparison with a matt paint, for example) and a lot of latex, must have the highest possible viscosity at a high shear gradient. This is known as Cone Plan viscosity or ICI viscosity, denoted $\mu_I$ (mPa·s). The thickening polyurethane of the present invention is entirely suited to aqueous compositions of this type.

The thickening polyurethane of the present invention can also be used in combination with a thickener of pseudoplastic type. Such a combination thus makes it possible to obtain a composition having a good dynamic behaviour related to the presence of the newtonian thickener and a good static behaviour related to the presence of the thickener of pseudoplastic type.

This novel thickener has, at the chain ends, hydrophobic groups of bicycloheptenyl type which are optionally polyalkoxylated.

HEUR Thickener

An object of the present invention relates to a thickener belonging to the category of the HEUR (Hydrophobically modified Ethoxylated URethanes). It concerns a non-ionic associative thickening polymer for aqueous compositions.

The thickening polyurethanes or HEUR of the present invention result from the reaction between a reactant which confers the associativity and which consists of an end hydrophobic group, a compound of polyol (for example poly(alkylene glycol)) type and a polyisocyanate. In the context of the present invention, the terms "reaction", "condensation" and "polycondensation" are used equivalently.

More specifically, it concerns a water-soluble thickening polyurethane resulting from the condensation:

a) of at least one polyethoxylated alcohol of formula (I):

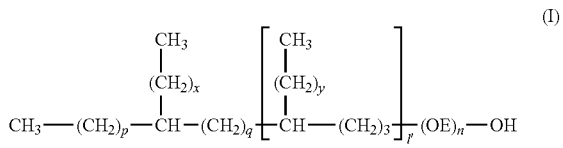

in which:
x and y represent, independently of one another, 0 or 1,
p, q, s and r are integers at least one of which is non zero,
$5<p+x+q+2r+yr+rs<11$ and
n represents an integer or a decimal number varying between 20 and 40, b) of at least one poly(alkylene glycol) and
c) of at least one polyisocyanate.

It is these novel polyurethanes which make it possible, for example, to thicken a paint composition at a high shear gradient (measurement of the ICI viscosity, for example).

The polyurethane according to the present invention comprises, as constituent a), a compound of formula (I). Such a compound is known, in the context of the present invention, as "ethoxylated associative compound comprising a carbon-based chain end and at least one methyl and/or ethyl branching".

The compounds of formula (I) comprise:
a polyethoxylated chain, itself consisting of from 20 to 40 ethoxylated units, for example of from 25 to 35 units,
a carbon-based chain end comprising from 8 to 14 carbon atoms, for example 12 carbon atoms and
at least one —$CH_3$ or —$CH_2$—$CH_3$ branching.

In the formula (I), the carbon-based chain comprises from 8 to 14 carbon atoms, for example 8, 9, 10, 11, 12, 13 or 14 carbon atoms.

This carbon-based chain can comprise a branching. In this case, r takes the value of zero. It can also comprise several branches, that is to say one or more r unit(s). The branchings can be of methyl (—CH$_3$) and/or ethyl (—CH$_2$—CH$_3$) type.

For the purposes of information, it is specified that, in the formula "5<p+x+q+2r+yr+rs<11":
"yr" means that the values y and r are multiplied together,
"rs" means that values y and r are multiplied together and
"2r" means that the value of r is doubled.

The water-soluble thickening polyurethane can result from the condensation of one or more polyethoxylated alcohol(s) of formula (I).

According to one embodiment of the present invention, the polyurethane consists of several polyethoxylated alcohols of formula (I). According to another embodiment, said polyurethane consists of just one polyethoxylated alcohol of formula (I).

According to one embodiment of the present invention, the polyethoxylated alcohol has a formula (II):

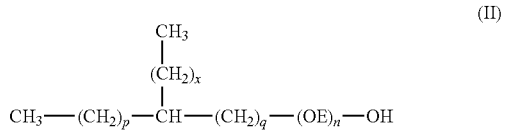
(II)

in which:
x represents 0 or 1,
p and q are integers at least one of which is non zero, 5<p+x+q<11 and
n represents an integer or a decimal number varying between 20 and 40.

According to this embodiment, the compounds of formula (II) comprise:
a polyethoxylated chain, itself consisting of from 20 to 40 ethoxylated units, for example of from 25 to 35 units,
a carbon-based chain end comprising from 8 to 14 carbon atoms, for example 12 carbon atoms and
a single —CH$_3$ or —CH$_2$—CH$_3$ branching.

According to another embodiment of the present invention, the polyethoxylated alcohol has the formula (III):

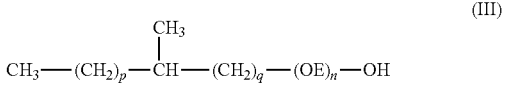
(III)

in which:
p and q are integers at least one of which is non zero, p+q=9 and
n represents an integer or a decimal number varying between 20 and 40.

According to this embodiment, the compounds of formula (III) comprise:
a polyethoxylated chain, itself consisting of from 20 to 40 ethoxylated units, for example of from 25 to 35 units,
a carbon-based chain end comprising from 8 to 14 carbon atoms, for example 12 carbon atoms and
a single —CH$_3$ branching (methyl branching).

Furthermore, the polyurethane comprises, as constituent b), a poly(alkylene glycol). "Poly(alkylene glycol)" is understood to mean a polymer of an alkylene glycol derived from an olefin oxide. The poly(alkylene glycol) chains of the constituent b) according to the present invention include a proportion of ethyleneoxy groups, a proportion of propyleneoxy groups and/or a portion of butyleneoxy groups. The poly(alkylene glycol) chains according to the present invention can, for example, comprise a dominant proportion of ethyleneoxy groups in combination with a secondary proportion of propyleneoxy groups. Specific examples of alkylene glycol polymers comprise: poly(alkylene glycol)s with an average molecular weight of 1,000 g/mol, 4,000 g/mol, 6,000 g/mol and 10,000 g/mol; polyethylene-polypropylene glycols with a percentage of ethylene oxide of between 20% and 80% by weight and a percentage of propylene oxide of between 20% and 80% by weight.

According to one aspect of the present invention, the polyurethanes result from the condensation in particular of a poly(alkylene glycol) which is poly(ethylene glycol). It can, for example, be a poly(ethylene glycol), the molecular mass of which varies between 2,000 g/mol and 20,000 g/mol, for example between 8,000 g/mol and 15,000 g/mol (limits included). Mention may be made, by way of example, of poly(ethylene glycol) (or PEG) with a molecular mass varying between 10,000 g/mol and 12,000 g/mol (limits included).

Furthermore, the polyurethane comprises, as constituent c), at least one polyisocyanate. "Polyisocyanate" is understood to mean a compound which comprises at least 2 isocyanate —N═C═O functional groups.

According to one aspect of the present invention, the polyurethanes result from the condensation in particular of a polyisocyanate which is chosen in the group consisting of toluene diisocyanate, toluene diisocyanate dimers, toluene diisocyanate trimers, 1,4-butane diisocyanate, 1,6-hexane diisocyanate, isophorone diisocyanate, 1,3-cyclohexane diisocyanate, 1,4-cyclohexane diisocyanate, 4,4'-diisocyanatodicyclohexylmethane, 1-methyl-2,4-diisocyanatocyclohexane, diphenylmethylene diisocyanate (MDI), for example 2,2'-MDI, 2,4'-MDI, 4,4'-MDI or their mixtures, dibenzyl diisocyanate, a mixture of 1-methyl-2,4-diisocymatocyclohexane and 1-methyl-2,6-diisocyanatocyclohexane, hexamethylene diisocyanate biuret, hexamethylene diisocyanate biuret dimers, hexamethylene diisocyanate biuret trimers and a mixture of at least two of these compounds.

According to one aspect of the invention, said polyurethane results from the condensation of:
a) from 1% to 29% by weight of at least one compound of formula (I), (II) and/or (III),
b) from 70% to 98% by weight of at least one poly(alkylene glycol) and
c) from 1% to 29% by weight of at least one polyisocyanate,
the sum of these mass percentages being equal to 100%.

According to another aspect of the invention, said polyurethane results from the condensation of:
a) from 3% to 10% by weight of at least one compound of formula (I), (II) and/or (III),
b) from 80% to 94% by weight of at least one poly(alkylene glycol) and
c) from 3% to 10% by weight of at least one polyisocyanate,
the sum of these mass percentages being equal to 100%.

According to one embodiment, the present invention relates to a water-soluble thickening polyurethane resulting exclusively from the condensation of the following 3 constituents:

a) a polyethoxylated alcohol of formula (I):

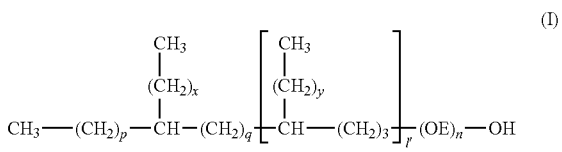

in which:
x and y represent, independently of one another, 0 or 1,
p, q, s and r are integers at least one of which is non zero,
$5 < p+x+q+2r+yr+rs < 11$ and
n represents an integer or a decimal number varying between 20 and 40,
b) a poly(alkylene glycol) and
c) a polyisocyanate.

The manufacture of the polyurethanes, which belong to the family of the thickeners of HEUR type, is known to the person skilled in the art, who may refer to the teaching of the documents cited above in the technological background of the present invention.

Another object of the present invention also relates to a method for the preparation of a polyurethane as described above, said method consisting of a condensation of its different constituents.

Formulation of the HEUR Thickener

The polyurethane according to the invention can be formulated or coformulated with other constituents or components.

Thus, the present invention also relates to an aqueous formulation comprising a polyurethane according to the invention, as described above.

This aqueous thickening formulation is intended to be incorporated in a final composition, for example a paint, a paper coating colour or a detergent composition.

The polyurethane according to the invention can be coformulated in the presence of water.

According to one embodiment, said aqueous formulation according to the invention consists of:
1) from 5% to 50% by weight of at least one polyurethane according to the invention, as described above, and
2) from 50% to 95% by weight of water,
the sum of these mass percentages being equal to 100%.

According to another embodiment, said aqueous formulation according to the invention consists of:
1) from 5% to 25% by weight of at least one polyurethane according to the invention, as described above, and
2) from 75% to 95% by weight of water,
the sum of these mass percentages being equal to 100%.

The polyurethane according to the invention can be coformulated in water, in the presence of at least one surface-active agent. This surface-active agent makes it possible to formulate the thickener in the form of a less viscous aqueous liquid solution which can thus be more easily used by the formulator.

Thus, according to one embodiment of the present invention, said aqueous formulation comprises a polyurethane, as described above, and also water and at least one surface-active agent.

"Surfactant" or "surface-active agent" is understood to mean a molecule or a polymer consisting of at least a hydrophilic part and of at least a hydrophobic part.

The surface-active agent used in the context of the invention can be different in nature; for example, it can be anionic or non-ionic.

This surfactant can be selected from the categories of ionic surfactants (in this case, preferably anionic surfactants) and/or non-ionic surfactants and/or mixed surfactants (comprising, in the same molecule, a non-ionic and anionic structure). The preferred surfactant is composed of at least one surface-active agent selected in the category of non-ionic surface-active agents, optionally in the presence of an anionic surface-active agent.

Mention may be made, among the suitable anionic surface-active agents, of sodium, lithium, potassium, ammonium or magnesium salts derived from alkyl ether sulphates with alkyl(s) varying from $C_6$ to $C_{12}$, in linear, iso, oxo, geminal, cyclic or aromatic configuration, or from $C_{12}$ alkyl sulphates, from alkyl phosphate esters or from dialkyl sulfosuccinates. The anionic surface-active agents are preferably used with at least one non-ionic surface-active agent.

Mention may be made, as examples of mixed surface-active agents, of alkoxylated alkylphenol sulfonates. The non-ionic surface-active agents can be used alone or in combination with an anionic surface-active agent. Mention may be made, as preferred examples of suitable non-ionic surface-active agents, of: ethoxylated (2 to 15 OE) $C_4$-$C_{18}$ alcohols, ethoxylated (2 to 40 OE) $C_4$-$C_{18}$ Guerbet alcohols, ethoxylated (2 to 40 OE) single-branched $C_{10}$-$C_{18}$ alcohols, $C_{18}$ sorbitol esters, ethoxylated (2 to 20 OE units) sorbitol esters, ethoxylated (less than 15 OE) $C_4$-$C_{18}$ acids, ethoxylated (30 to 40 OE) castor oil, ethoxylated (7 to 60 OE) hydrogenated castor oil, esters such as glycerol palmitate, glycerol stearate, ethylene glycol stearate, diethylene glycol stearate, propylene glycol stearate, polyethylene glycol 200 stearate and ethoxylated (2 to 15 OE) $C_{18}$ esters. The hydrophobic chains can correspond to linear, iso, oxo, cyclic or aromatic structures.

According to one embodiment, the formulation comprises at least one non-ionic surface-active agent optionally combined with at least one anionic surface-active agent, at a total content by weight ranging from 0.1% to 40% by weight, for example from 5% to 20% by weight or from 10% to 17% by weight. In this case, the ratio by weight between the two surface-active agents can, for example, vary between 25/75 and 75/25. According to one embodiment of the present invention, the polyurethane of the present invention is formulated in the presence of more than two surface-active agents, for example three or four surface-active agents.

According to one embodiment, said aqueous formulation according to the invention consists of:
1) from 2% to 50% by weight of at least one polyurethane according to the invention, as described above, preferably from 5% to 30% by weight,
2) from 0.1% to 40% by weight of at least one surface-active agent, preferably from 5% to 30% by weight and
3) from 10% to 93% by weight of water, preferably from 40% to 85% by weight,
the sum of these mass percentages being equal to 100%.

The polyurethane according to the invention can be formulated in a water-miscible solvent. The main reason for the addition of an organic cosolvent is to lower the viscosity of this polyurethane in the water, in order to facilitate the handling. The polyurethane is, for example, formulated with one or more polar solvent(s) belonging in particular to the group consisting of water, methanol, ethanol, propanol, isopropanol, butanols, acetone, tetrahydrofuran or their mixtures.

Two specific examples of water-miscible organic solvents are:
diethylene glycol monobutyl ether (also known under the name of Butyl Carbitol™) or ethylene or propylene glycol ether and
butylene glycol ether.

The viscosity of the polyurethane as it is, before it is incorporated in a paint composition, for example, is advantageously less than 10,000 mPa·s at 25° C. and at 100 revolutions per minute, so that it is easier to pour from the storage container and more rapidly incorporated in the composition to be thickened at room temperature. The water-miscible solvent chosen for such commercial compositions has, to date, exclusively been an organic solvent.

The polyurethane according to the invention can be coformulated in water, in the presence of a coalescent agent. Equivalently to a solvent, the coalescent agent makes it possible to formulate the thickener in the form of a less viscous aqueous liquid solution which can thus be more easily used by the formulator.

According to one embodiment, said aqueous formulation according to the invention consists of:
1) from 5% to 50% by weight of at least one polyurethane according to the invention, as described above,
2) from 5% to 30% by weight of at least one solvent and/or coalescent agent and
3) from 20% to 75% by weight of water,
the sum of these mass percentages being equal to 100%.

According to one aspect of the invention, the aqueous formulation further comprises at least one additive selected in the group consisting of a biocide, a solvent, an anti-foaming agent, a pH regulator, a coalescent agent, an encapsulating agent and their mixtures.

"Biocide" is understood to mean a chemical substance intended to destroy, repel or render inoffensive harmful organisms, to prevent the action thereof or to combat them in any other way, by chemical or biological action.

"Anti-foaming agent" is understood to mean a substance or a formulation intended to destroy air bubbles within a homogeneous or heterogeneous liquid medium (or at its surface) or to prevent their formation.

"pH regulator" or "pH-regulating agent" is understood to mean a chemical compound which makes it possible to adjust the pH to the expected value. For example, the pH-regulating agent can increase the pH; this is the case with bases, such as NaOH. Alternatively, the pH-regulating agent can decrease the pH; this is the case with acids.

"Coalescent agent" is understood to mean an agent used in paints which makes it possible to lower the paint Minimum Film Formation Temperature (MFFT) to a temperature suited to the application conditions desired (for example an MFFT of 5° C. for an external application). Mention may be made, as examples of coalescent agents according to the invention, of propylene glycol, butyl glycol, 2,2,4-trimethyl-1,3-pentanediol monoisobutyrate or 2,2,4-trimethyl-1,3-pentanediol diisobutyrate, 2,2,4-trimethyl-1,3-pentanediol monoisobutyrate, glycol ether derivatives of Dowanol® type.

"Encapsulating agent" is understood to mean an agent which creates a hydrophobic environment, for example a solvation cage. Mention may in particular be made, as encapsulating agent, of cyclodextrin.

According to one embodiment, said aqueous formulation according to the invention consists of:
1) from 2% to 50% by weight of at least one polyurethane according to the invention, as described above, preferably from 2% to 30% by weight,
2) from 0.1% to 40% by weight of at least one surface-active agent, preferably from 5% to 30% by weight,
3) from 10% to 93% by weight of water, preferably from 40% to 85% by weight and
4) from 0% to 5% by weight of at least one other additive chosen in the group consisting of a biocide, a solvent, an anti-foaming agent, a pH regulator, a coalescent agent, an encapsulating agent and their mixtures, preferably from 0.5% to 4% by weight,
the sum of these mass percentages being equal to 100%.

Final Aqueous Composition and Uses of the Polyurethane

An object of the present invention is an aqueous composition comprising a polyurethane according to the invention or an aqueous thickening formulation according to the invention, said final aqueous composition being selected in the group consisting of a paint, a putty, a thick coating, a waterproof coating, a lacquer, a varnish, an ink, a slurry, a paper coating colour, a cosmetic formulation and a detergent formulation.

Said composition is thickened using a polyurethane or an aqueous thickening formulation according to the invention.

Furthermore, the present invention also relates to the use of a polyurethane according to the invention or of an aqueous formulation according to the invention for thickening an aqueous composition, said aqueous composition being selected in the group consisting of a lacquer, a varnish, a paint, a putty, a thick coating, a waterproof coating, an ink, a slurry, a paper coating colour, a cosmetic composition and a detergent composition. According to one embodiment, the aqueous composition to be thickened is of the following types: gloss paint, semi-gloss paint, satin paint or all other paints with a low Pigment Volume Concentration (PVC).

The "pigment volume concentration" is defined by the following formula:

$$\text{PVC (\%)} = 100 \times V_f / (V_f + V_b)$$

with $V_f$ which represents the volume of the mineral fillers and
$V_b$ which represents the volume of binders in the paint formulation.

According to another embodiment, the aqueous composition to be thickened is of the following type: paint comprising a medium or high Pigment Volume Concentration (PVC), varying between egg-shell paint and matt paint. In this case, the thickening polyurethane of the present invention can be combined with another thickener having a pseudoplastic profile.

According to an embodiment of the present invention, said polyurethane or said aqueous polyurethane formulation is used as a levelling agent of said aqueous composition. The polyurethane according to the invention makes it possible, for example, to increase the levelling value of the paint which contains it, that is to say the self-smoothing ability of the paint during the application. This value can, for example, be measured on a contrast chart Leneta, ASTM D4062 standard, "flow & levelling".

According to one aspect of the present invention, the aqueous composition comprises from 0.02% to 5% by weight of active ingredient of said thickener.

According to another aspect of the present invention, the aqueous formulation comprises from 0.05% to 2% by weight of active ingredient of said thickener.

"Weight of active ingredient" is understood to mean the dry weight of polyurethane according to the invention, independently of the coformulation ingredients.

According to yet another aspect of the present invention, the aqueous composition comprises at least one mineral filler selected in the group consisting of calcium carbonate, kaolin, talc and silicate and/or at least one pigment selected in the group consisting of titanium dioxide, iron oxide and zinc.

According to one aspect of the invention, the aqueous composition is a paint and comprises at least one dispersing agent, at least one mineral pigment or filler, at least one binder, at least one biocide, at least one anti-foaming agent and optionally one surface-active agent, a surface agent and/or a coalescent agent, a solvent.

The examples which follow make possible a better understanding of the present invention, without limiting the scope thereof.

EXAMPLES

The viscosity of the test formulations or of the paint compositions is determined at different rate gradients:
at a low rate gradient: the Brookfield viscosity (Bk), which is measured using a RVT-type Brookfield viscometer, in the unstirred flask, at a temperature of 25° C. and at two rotational speeds of 10 and 100 revolutions per minute with the appropriate spindle. Reading is carried out after rotating for one minute. Two Brookfield viscosity measurements, respectively denoted $\mu_{Bk10}$ and $\mu_{Bk100}$ (mPa·s), are thus obtained,
at a medium rate gradient, the Stormer viscosity, denoted $\mu_S$ (Krebs units or Kμ) and
at a high rate gradient: the Cone Plan viscosity or ICI viscosity, denoted $\mu_I$ (mPa·s).

Example 1

This example illustrates the use of a thickener according to the invention in a solvent-free aqueous satin paint formulation, the composition of which is given in Table 1 below.

It illustrates the thickening power of a polyurethane according to the invention (tests 1-3 and 2-3), using a compound of formula (III). At the same time, this example also illustrates polyurethanes outside the invention (tests 1-1 and 2-1) and a HASE acrylic thickener outside the invention (tests 1-2 and 2-2).

Tests 1-1 and 2-1 (Outside the Invention)

Said polyurethane results from the condensation of, expressed as percentage by weight with respect to the total weight of the polyurethane:
18.6% by weight of an alcohol of formula $CH_3$—$(CH_2)_{11}$-$(OE)_{30}$-OH,
77.5% by weight of PEG 10 000 and
3.9% by weight of isophorone diisocyanate (IPDI).

Tests 1-2 and 2-2 (Outside the Invention)

These tests use an HASE acrylic thickener consisting of, expressed as percentage by weight with respect to the total weight of the compound:
35.1% by weight of methacrylic acid,
52.8% by weight of ethyl acrylate and
12.1% by weight of a monomer which is the methacrylate of oxo-C12-$(OE)_{30}$, that is to say a methacrylate monomer comprising 30 ethylene oxide units and a hydrophobic chain end of $CH_3$—$(CH_2)_p$—$CH(-CH_3)$—$(CH_2)_q$ type with p+q=9.

Such a thickener corresponds to a compound as described in the document WO 2011/104599.

Tests 1-3 and 2-3 (According to the Invention)

Said polyurethane results from the condensation of, expressed as percentage by weight with respect to the total weight of the polyurethane:
21.9% by weight of a compound of formula (III):

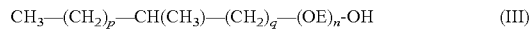

$$CH_3-(CH_2)_p-CH(CH_3)-(CH_2)_q-(OE)_n-OH \quad (III)$$

in which:
p+q=9,
n is equal to 30,
74.5% by weight of PEG 10 000 and
3.6% by weight of isophorone diisocyanate (IPDI).

The polyurethanes are formulated in water in the presence of a surface-active agent which is a $C_8$-$C_{10}$ fraction of an alkoxylated fatty alcohol (Simulsol® OX1008). The PU/surfactant/water ratios are 20/5/75.

All the results have been combined in Tables 2 and 3 below.

For each of the tests, the $\mu_{Bk10}$, $\mu_{Bk100}$, $\mu_I$ (in mPa·s) and $\mu_S$ (in Krebs units measured with the standard module) viscosities were determined according to the methods described above at T=0 and at T=24 h at room temperature.

TABLE 1

| Constituent of the paint (g) | Weight (g) |
|---|---|
| Water | 99.45 |
| Dispersant (Coadis ® BR3) | 3.9 |
| Biocide (Acticide ® MBS) | 1.3 |
| Anti-foaming agent (Airex® 901W) | 1.31 |
| NH$_4$OH (28%) | 0.5 |
| TiO$_2$ (RHD2) | 122.2 |
| CaCO$_3$ (Omyacoat® 8500G) | 84.5 |
| Binder (Acronal 290D) | 270.6 |
| Monopropylene glycol | 6.5 |
| Texanol | 6.5 |
| Anti-foaming agent (Tego ® 825) | 0.65 |
| PU thickener (according to the tests) | Series 1: 28.6 Series 2: variable (see Table 3) |
| Water | q.s.p for 650 g in total |

TABLE 2

|  |  | Test 1-1 OInv | Test 1-2 OInv | Test 1-3 INV |
|---|---|---|---|---|
| Dose (% by weight/total formula) |  |  | 0.88 |  |
| T = 0 | $\mu_{Bk10}$ | 2,135 | 66,000 | 1,590 |
|  | $\mu_{Bk100}$ | 1,160 | 16,680 | 835 |
|  | $\mu_S$ | 86 | >141 | 78 |
|  | $\mu_I$ | 1.6 | 2.9 | 1.6 |
| T = 24 h | $\mu_{Bk10}$ | 2,320 | 74,700 | 1,720 |
|  | $\mu_{Bk100}$ | 1,296 | 18,600 | 946 |
|  | $\mu_S$ | 89 | >141 | 81 |
|  | $\mu_I$ | 1.6 | 2.95 | 1.6 |

TABLE 3

|  |  | Test 2-1 OInv | Test 2-1 Oinv | Test 2-2 Oinv | Test 2-3 INV |
|---|---|---|---|---|---|
| Dose | (% by weight/total formula) | 1.44 | 1.24 | 0.506 | 1.44 |
| T = 0 | $\mu_{Bk10}$ | 3,030 | 3,040 | 24,200 | 2,190 |
|  | $\mu_{Bk100}$ | 1,706 | 1,678 | 6,240 | 1,230 |
|  | $\mu_S$ | 96 | 96 | 127 | 88 |
|  | $\mu_I$ | 3.4 | 2.8 | 1.6 | 2.8 |

TABLE 3-continued

|   |   | Test 2-1 OInv | Test 2-1 Oinv | Test 2-2 Oinv | Test 2-3 INV |
|---|---|---|---|---|---|
| T = 24 h | $\mu_{Bk10}$ | 3,580 | 3,560 | 29,250 | 2,550 |
|   | $\mu_{Bk100}$ | 2,090 | 2,060 | 7,495 | 1,448 |
|   | $\mu_S$ | 102 | 101 | 135 | 92 |
|   | $\mu_I$ | 3.4 | 2.8 | 1.6 | 2.8 |

OInv: Outside the Invention
INV: According to the INVention

The polyurethane according to the present invention (tests 1-3 and 2-3) has a rheological profile of newtonian type: low viscosity at low shear gradient.

By comparison of the results presented of tests 1-3 and 2-3 (according to the invention), a significantly improved thickening at a high rate gradient (1.4) is observed in the paint formulation, whereas the Brookfield and Stormer viscosities are changed more moderately; this is characteristic of a newtonian thickener, "ICI builder" type, which makes possible selective increase in the ICI viscosity as a function of the dose.

The polyurethane of the present invention thus offers a good compromise between newtonian behaviour (which makes it possible to obtain low viscosities at a low shear gradient and at a medium shear gradient) and "ICI builder" characteristic, which makes possible a selective increase in the ICI viscosity as a function of the dose used. The formulator can thus adjust the dose of thickener as a function of the rheological behaviour desired at a high shear gradient.

The polyurethane outside the invention of test 1-1 makes it possible to obtain a thickening at a high rate gradient (1.4) which is identical to that obtained with the polyurethane according to the invention of test 1-3. Nevertheless, it is observed that the Brookfield and Stormer viscosities obtained with the polyurethane outside the invention of test 1-1 are overall higher than those obtained with the polyurethane according to the invention of test 1-3 at an identical dose (0.88% by weight, with respect to the total weight of the composition).

The polyurethane of tests 1-1 and 2-1 generates an ICI viscosity which can be modulated as a function of the dose added to the formula but it is coupled to excessively high viscosities at low and at medium rate gradients. The profile of this polyurethane is not sufficiently newtonian.

As regards test 2-1a, the polyurethane dose is adjusted in order to obtain an ICI viscosity identical to that of test 2-3 and thus to be able to compare the viscosities at low and medium rate gradients. It is observed that the viscosities obtained at low and medium shear gradients remain too high.

The invention claimed is:

1. A water-soluble thickening polyurethane, obtained by reacting a mixture comprising:
   a poly(alkylene glycol) having a molecular mass in a range of from 2,000 to 20,000 g/mol;
   a polyisocyanate; and
   a polyethoxylated alcohol of formula (III):

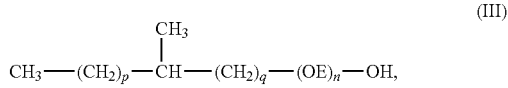

wherein
p and q are integers at least one of which is non zero,
p+q=8 or 9, and
n is an integer or a decimal number in a range of from 25 to 40.

2. The polyurethane of claim 1, obtained by condensing:
   (a) at least one of the polyethoxylated alcohol of formula (III) in a range of from 1 to 29 wt. %;
   (b) at least one of the poly(alkylene glycol) in a range of from 70 to 98 wt. %; and
   (c) at least one of the polyisocyanate in a range of from 1 to 29 wt. %,
   wherein a sum of mass percentages of (a), (b), and (c) is equal to 100%.

3. An aqueous formulation, comprising:
   the water-soluble thickening polyurethane of claim 1; and
   water.

4. The aqueous formulation of claim 3, further comprising:
   a surface-active agent.

5. The aqueous formulation of claim 3, further comprising:
   a biocide, a solvent, an anti-foaming agent, a pH regulator, a coalescent agent, and/or an encapsulating agent.

6. The aqueous formulation of claim 3, consisting of:
   (a) at least one of the water-soluble thickening polyurethane in a range of from 2 to 50 wt. %;
   (b) at least one surface-active agent in a range of from 0.1 to 40 wt. %;
   (c) the water in a range of from 10 to 93 wt. %; and
   (d) at least one additive selected from the group consisting of a biocide, a solvent, an anti-foaming agent, a pH regulator, a coalescent agent, and an encapsulating agent, in a range of from 0 to 5 wt. %,
   wherein a sum of mass percentages of (a), (b), (c), and (d) is equal to 100%.

7. A method for thickening an aqueous composition, the method comprising:
   contacting the aqueous composition with the water-soluble thickening polyurethane of claim 1,
   wherein the aqueous composition is a lacquer, a varnish, a paint, a putty, a thick coating, a waterproof coating, an ink, a slurry, a paper coating color, a cosmetic composition, or a detergent composition.

8. An aqueous composition, comprising:
   the water-soluble thickening polyurethane of claim 1 as a levelling agent,
   wherein the aqueous composition is a lacquer, a varnish, a paint, a putty, a thick coating, a waterproof coating, an ink, a slurry, a paper coating color, a cosmetic composition, or a detergent composition.

9. A method for thickening an aqueous composition, the method comprising:
   contacting the aqueous composition with the aqueous formulation of claim 3,
   wherein the aqueous composition is a lacquer, a varnish, a paint, a putty, a thick coating, a waterproof coating, an ink, a slurry, a paper coating color, a cosmetic composition, or a detergent composition.

10. An aqueous composition, comprising:
    the aqueous formulation of claim 3 as a levelling agent,
    wherein the aqueous composition is a lacquer, a varnish, a paint, a putty, a thick coating, a waterproof coating, an ink, a slurry, a paper coating color, a cosmetic composition, or a detergent composition.

11. The polyurethane of claim 1, wherein, in the polyethoxylated alcohol of formula (III), wherein p and q sum to 8.

12. The polyurethane of claim 1, wherein, in the polyethoxylated alcohol of formula (III), wherein p and q sum to 9.

13. The polyurethane of claim 1, wherein, in the polyethoxylated alcohol of formula (III), wherein n is in a range of from more than 30 to 40.

14. The polyurethane of claim 11, wherein, in the polyethoxylated alcohol of formula (III), wherein n is in a range of from more than 30 to 40.

15. The polyurethane of claim 12, wherein, in the polyethoxylated alcohol of formula (III), wherein n is in a range of from 25 to 35.

16. The polyurethane of claim 11, wherein, in the polyethoxylated alcohol of formula (III), wherein n is in a range of from 25 to 35.

17. The polyurethane of claim 1, wherein, in the polyethoxylated alcohol of formula (III), wherein n is in a range of from 25 to 35.

18. The polyurethane of claim 1, wherein, in the polyethoxylated alcohol of formula (III) wherein n is in a range of from 30 to 40.

19. The polyurethane of claim 11, wherein, in the polyethoxylated alcohol of formula (III), wherein n is in a range of from 30 to 40.

20. The polyurethane of claim 1, wherein, in the polyethoxylated alcohol of formula (III), wherein n is in a range of from more than 30 to 40.

* * * * *